(12) United States Patent
Shawl (10) Patent No.: US 11,612,784 B2
(45) Date of Patent: Mar. 28, 2023

(54) MULTI-MODAL REHABILITATION DEVICE AND METHODS

(71) Applicant: Theodros Shawl, Oakland, CA (US)

(72) Inventor: Theodros Shawl, Oakland, CA (US)

( * ) Notice: Subject to any disclaimer, the term of this patent is extended or adjusted under 35 U.S.C. 154(b) by 0 days.

(21) Appl. No.: 16/952,042

(22) Filed: Nov. 18, 2020

(65) Prior Publication Data

US 2022/0152451 A1    May 19, 2022

(51) Int. Cl.

| | |
|---|---|
| A63B 23/08 | (2006.01) |
| A61F 5/01 | (2006.01) |
| A63B 21/04 | (2006.01) |
| A63B 21/055 | (2006.01) |
| A63B 23/035 | (2006.01) |
| A63B 21/00 | (2006.01) |
| A61H 15/00 | (2006.01) |
| A63B 22/00 | (2006.01) |

(52) U.S. Cl.
CPC ............ *A63B 23/08* (2013.01); *A61F 5/0123* (2013.01); *A61H 15/00* (2013.01); *A63B 21/0428* (2013.01); *A63B 21/0552* (2013.01); *A63B 21/4034* (2015.10); *A63B 21/4047* (2015.10); *A63B 23/03508* (2013.01); *A61F 2005/0158* (2013.01); *A61H 2201/1261* (2013.01); *A61H 2205/12* (2013.01); *A63B 2022/0094* (2013.01)

(58) Field of Classification Search
CPC . A63B 23/08; A63B 21/0428; A63B 21/0552; A63B 21/4034; A63B 21/4047; A63B 23/03508; A63B 2022/0094; A61F 5/0123; A61F 2005/0158; A61H 15/00; A61H 2201/1261; A61H 2205/12; A61H 1/024; A61H 9/0078; A61H 2015/0021; A61H 2201/0107; A61H 2201/164; A61H 2201/165; A61H 2201/1671; A61H 2201/1676; A61H 2201/02
See application file for complete search history.

(56) References Cited

U.S. PATENT DOCUMENTS

| | | | | |
|---|---|---|---|---|
| 3,805,773 | A | * | 4/1974 | Sichau ................... A61F 5/0127 602/28 |
| 4,494,534 | A | * | 1/1985 | Hutson .................. A61F 5/0125 602/23 |
| 4,869,499 | A | * | 9/1989 | Schiraldo ........... A63B 21/4011 482/79 |
| 4,922,892 | A | * | 5/1990 | Akcelrod ........... A63B 23/0417 601/34 |

(Continued)

*Primary Examiner* — Garrett K Atkinson
(74) *Attorney, Agent, or Firm* — Craige Thompson; Thompson Patent Law; Timothy D. Snowden (57) ABSTRACT

Apparatus and methods relate to a multi-modal rehabilitation device having a reconfigurably lockable, adjustable knee stabilizer and a removable foot plate provided with removable resistance elements. In an illustrative example, the resistance elements may be repositionable. The foot plate may be provided with rollers. The rollers may be configured for use in gliding exercises. The rollers may be configured for self-massage therapy. The rollers may be removable. The rollers may be disposed in a removable leg band which may be disposed around a leg of a user. In an illustrative example, the device further includes a graduated self-deflating thermal-compression device. Various embodiments may provide multiple therapy modalities in an efficient, economical, and user-friendly device.

20 Claims, 9 Drawing Sheets

(56) References Cited

U.S. PATENT DOCUMENTS

| | | | | |
|---|---|---|---|---|
| 5,330,417 | A * | 7/1994 | Petersen | A63B 21/4025 601/33 |
| 5,788,618 | A * | 8/1998 | Joutras | A63C 10/145 482/8 |
| 5,976,063 | A * | 11/1999 | Joutras | A63B 21/4025 482/8 |
| 6,770,040 | B2 * | 8/2004 | Perner | A61H 1/0266 601/5 |
| 8,475,397 | B2 * | 7/2013 | Chiu | A61F 5/0127 602/17 |
| 8,945,028 | B2 * | 2/2015 | Kazerooni | A61H 3/00 601/5 |
| 9,180,037 | B1 * | 11/2015 | Smith | A61F 5/0111 |
| 9,375,377 | B1 * | 6/2016 | Edwards | A61F 5/0123 |
| 10,576,620 | B1 * | 3/2020 | Chou | A61F 5/0102 |
| 11,312,003 | B1 * | 4/2022 | Chou | A63B 71/1225 |
| 11,318,602 | B1 * | 5/2022 | Chou | B25J 9/104 |
| 11,337,879 | B2 * | 5/2022 | Shuch | A61H 9/0092 |
| 2002/0193210 | A1 * | 12/2002 | Turner | A63B 21/4047 482/80 |
| 2004/0102723 | A1 * | 5/2004 | Horst | A61H 3/008 601/5 |
| 2008/0108917 | A1 * | 5/2008 | Joutras | A61H 1/02 601/34 |
| 2009/0292369 | A1 * | 11/2009 | Kazerooni | A61H 3/061 128/845 |
| 2011/0172578 | A1 * | 7/2011 | Chiu | A61F 5/0127 602/28 |
| 2013/0102935 | A1 * | 4/2013 | Kazerooni | B25J 9/0006 601/35 |
| 2013/0197408 | A1 * | 8/2013 | Goldfarb | A61H 1/024 601/35 |
| 2014/0088466 | A1 * | 3/2014 | Hansen | A61G 13/009 482/129 |
| 2014/0094721 | A1 * | 4/2014 | Diallo | A63B 24/0087 601/5 |
| 2014/0142475 | A1 * | 5/2014 | Goldfarb | A61H 1/0262 601/35 |
| 2017/0049659 | A1 * | 2/2017 | Farris | B25J 9/104 |
| 2017/0135841 | A1 * | 5/2017 | Bonutti | A61F 5/0127 |
| 2017/0354525 | A1 * | 12/2017 | Rybchinskya | A61F 5/0104 |
| 2017/0367866 | A1 * | 12/2017 | Robinson | A61F 5/0127 |
| 2019/0308059 | A1 * | 10/2019 | Wortham | A63B 23/03508 |
| 2019/0358071 | A1 * | 11/2019 | Hatzis | A61F 5/0113 |
| 2020/0038216 | A1 * | 2/2020 | Hanna | A61F 5/0123 |
| 2020/0069505 | A1 * | 3/2020 | Fujita | A61H 1/02 |
| 2020/0206065 | A1 * | 7/2020 | Yang | A61H 1/0237 |
| 2020/0337931 | A1 * | 10/2020 | Shuch | A61H 1/0266 |
| 2021/0052931 | A1 * | 2/2021 | Louis | A63B 21/065 |
| 2021/0196551 | A1 * | 7/2021 | Burke | A61H 1/024 |
| 2022/0184450 | A1 * | 6/2022 | Louis | A63B 23/08 |

* cited by examiner

MULTI-MODAL REHABILITATION DEVICE AND METHODS

TECHNICAL FIELD

Various embodiments may relate to the field of rehabilitation and physical therapy. Specifically, embodiments may relate to apparatus for rehabilitation and methods thereof, including post-surgery knee rehabilitation, as well as rehabilitation and physical therapy related to the lower limbs.

BACKGROUND

In the United States, there are an estimated seven hundred thousand to one million knee replacement procedures per year. There are expected to be nearly three and one-half million procedures per year by 2030 in the United States. In the Asia-Pacific region, it is expected that nearly two and one-half million procedures will be performed by 2024.

SUMMARY

Apparatus and methods relate to a multi-modal rehabilitation device having a reconfigurably lockable, adjustable knee stabilizer and a removable foot plate provided with removable resistance elements. In an illustrative example, the resistance elements may be repositionable. The foot plate may be provided with rollers. The rollers may be configured for use in gliding exercises. The rollers may be configured for self-massage therapy. The rollers may be removable. The rollers may be disposed in a removable leg band which may be disposed around a leg of a user. In an illustrative example, the device further includes a graduated self-deflating thermal-compression device. Various embodiments may provide multiple therapy modalities in an efficient, economical, and user-friendly device.

Various embodiments may have one or more advantages. For example, some implementations provide some combination of adjustable position knee support, stabilization, compression therapy, thermal therapy, passive and active range of motion and strengthening therapy. In some examples, the user may use a single device for post-surgery or post-injury recovery and rehabilitation. In some examples, a single multi-modal device may be used during therapy, resting, sitting, and locomotion. In some examples, the knee stabilizer and leg band with rollers may advantageously provide for knee flexion exercises. In some examples, the rollers may advantageously provide for massage therapy and may advantageously disperse swelling around a lower extremity of the leg resulting from injury or insult such as surgery. In some examples, the the thermal-compression device may advantageously combat prolonged and sustained compression and so promote proper fluid flow.

BRIEF DESCRIPTION OF THE DRAWINGS

Various embodiments of the present embodiments are described with reference to the following figures. Like reference numerals therein refer to like parts throughout the various views unless otherwise specified. Embodiments and portions of embodiments illustrated and described herein are non-limiting and non-exhaustive.

DETAILED DESCRIPTION OF ILLUSTRATIVE EMBODIMENTS

The following description of various embodiments, combined with the associated drawings, enables persons of ordinary skill in the art to both practice preferred embodiments, and to understand related applications and embodiments that may not be specifically set forth, but are encompassed by the specification and claims.

Embodiments disclosed herein may relate to multi-modal rehabilitation apparatus and methods, combining various rehabilitation and therapy modalities. In some embodiments, the device may include a multi-position lockable knee stabilizer, and a removable and adjustable foot plate. The knee stabilizer and foot plate, together, may be configured to provide rehabilitation and physical therapy modalities including, but not limited to:
  adjustable position knee support,
  relocatable transitory compression therapy,
  bi-modal thermal therapy, including, for example, with inflatable compression and gradual release (deflation) to avoid over-compression,
  passive range of motion (ROM) therapy and passive progressive ROM therapy,
  active ROM therapy (e.g., knee glide therapy with removable, relocatable, multi-use rollers), and
  strengthening exercise therapy (e.g., using relocatable and multi-use roller/weights).

Various embodiments herein include methods of use of such apparatus, at least for the modalities described above, and combinations thereof.

Various embodiments may provide advantages in ease of use, economy, convenience in sourcing, and multi-modal use vs fractionated, inconvenient, and expensive sourcing, assembly, storage, and use of a plethora of devices. For example, various embodiments may advantageously replace a combination of modalities for rehabilitation and therapy after major knee injury or surgery, which may include, by way of example and not limitation:
  rectangular, wedge, or other shaped pillow for adjustable support in various positions, which may cost on the order of one hundred dollars;
  an ice therapy machine or similar means of providing localized cold therapy, which may cost on the order of four hundred dollars, and potentially separate means of compression, such as to prevent deep vein thrombosis (DVT);
  a controlled range knee exercise machine for muscle and joint exercise, as well as DVT prevention, which may currently cost on the order of one hundred dollars, or another suitable active exercise apparatus;

a continuous passive motion (CPM) machine for passive range of motion therapy, which may currently cost on the order of eight-hundred and fifty dollars per month for rental, or over two-thousand dollars for purchase, and so often unnecessarily avoided by surgeons and physical therapists due to cost concerns;

a post-operative knee brace, which may cost on the order of five hundred dollars; and miscellaneous exercise and strengthening products, such as bands and weights, which may currently cost on the order of fifty to one hundred dollars, or more.

Overall, embodiments combining such modalities may save hundreds to thousands of dollars, and may alleviate problems in sourcing, assembling, maintaining, storing, and using the plethora of equipment.

Exemplary Components

Various embodiments may include the following exemplary components. Various combinations of the different elements as herein defined may be appropriate, for example, for specific applications and environments of use. Specific examples and embodiments of the apparatus and methods will serve to illustrate to persons skilled in the art the broader concepts disclosed.

Knee Stabilizer

In various embodiments, the knee stabilizer may include a plurality of frame members, having upper and lower portions, oriented substantially parallel with the leg. The upper and lower portions of the stabilizer frame members may each be joined with a lockable hinge which has both an unlocked mode in which the hinge rotates freely, and a locked mode in which the hinge is held in one of a plurality of static angular positions.

Extension

In various embodiments, the knee stabilizer may be extendable in length on at least one of the portions above or below the lockable hinges (e.g., both upper stabilizer frame members extend, both lower stabilizer frame members extend); in some embodiments, the knee stabilizer may be extendable in length on both sides of the lockable hinges. In some such embodiments, the adjustability may be provided by an inner frame member, such as a rail, tube, or similar elongate structure, which slides inside an outer frame member, such as a tube, a channel (such as a c-channel), or similar structure. In some embodiments, the inside and outer frame members may be substantially or actually identical, but oriented, e.g. one hundred eighty degrees around the longitudinal axis in reference to one another, and configured with mating features. In various embodiments, the inner and outer frame members may be lockable at a plurality of extension points, such as by detents, sliding friction between the frame members, lock screws, locking cams, pins, bolts, other suitable components, or some combination thereof.

Attachment to Foot Plate

In various embodiments, the knee stabilizer may be provided with at least one attachment point for a detachable foot plate, the attachment point being disposed at the distal end of at least one of the stabilizer frame members' lower portions. In some such embodiments, the foot plate may be adjustably engageable in the knee stabilizer, such as by the lower portions of the stabilizer frame members being provided with tubes or other appropriate structures to receive mating plate frame members a variable amount. Similar structures, adjustability, and locking components as were described in relation to extension of the knee stabilizer itself may be provided in various embodiments. In some embodiments of the knee stabilizer capable of receiving a detachable foot plate, the attachment points may not leave sharp or uncomfortable edges exposed when the foot plate is detached. In various embodiments, when the foot plate is detached, the knee stabilizer may be configured such that a user may simply secure the stabilizer on a distal aspect of the lower leg and the proximal aspect of the upper leg to stabilize the knee while maneuvering.

Integral Structure Embodiments

In various embodiments, the plurality of upper frame members and plurality of lower frame members, respectively, may be connected together to form integral structures having various features integrated thereinto, such as lockable hinges, adjustable extensions, receiving mechanisms for the foot plate, etc. In some embodiments, a plurality of straps, whether rigid, semi-rigid, flexible, elastic, or some combination thereof, may be provided at least between a first and second stabilizer frame member, thereby connecting them together such that the stabilizer frame members can be situated along a user's leg to support the leg and knee.

Material

In various embodiments, the knee stabilizer may include metal, polymeric, other suitable materials, or some combination thereof. In some embodiments, at least some contact surfaces may be provided with enhanced comfort coatings, whether permanent, semi-permanent, removable, or some combination thereof. Example such coatings include, but are not limited to, neoprene rubber, neoprene foam, polyurethane rubber, polyurethane foam, vinyl, foam, rubber, fabric, and felt.

Modalities

In various embodiments, the knee stabilizer may be capable of facilitating a plurality of modalities. The knee stabilizer may be provided, in some embodiments, with straps or other suitable securing means, to secure the user's leg in the knee stabilizer, above and below the knee. Such straps include, but are not limited to: hook-and-loop straps, e.g. having hook fabric on one end and loop fabric on the opposite side of the other; elastic straps, buckle straps, snapped straps, and spring-loaded bars.

Thus, the knee stabilizer, in some configurations, may provide a support modality, or a passive ROM modality, or combinations thereof, in which the leg is secured within the knee stabilizer above and below the knee. The knee stabilizer, in some configurations, may provide a lower limb active ROM modality, foot massage modality (e.g., to reduce swelling and facilitate blood flow, to assist in and/or encourage knee glide exercises), or some combination thereof. In some configurations it may facilitate a strengthening therapy modality, when the lower leg is left unstrapped or loosely strapped, and the user moves their foot backwards and forwards (e.g., on the rollers), while still receiving knee support modality. For example, knee glide exercises may be an integral aspect of post-surgical and/or post-injury rehabilitation. Embodiments configured for knee glide exercises may accordingly advantageously promote, by way of example and not limitation, enhanced movement within the joint space to increase strength, circulate fluid trapped as a result of inflammatory response, reduce scar tissue formation, or some combination thereof.

In some configurations, the knee stabilizer may provide an active ROM modality when the knee hinges are unlocked, and the user's leg is strapped above and below the knee, and the user can move their leg back and forth. In some configurations, the knee stabilizer may provide a passive ROM modality when the knee hinges are locked, and the user's leg is strapped above and blow the knee. In some configurations, particularly when the leg is secured above and below the knee, the knee stabilizer may provide a passive progressive ROM modality when the knee hinges are locked in a desired angle of flexion. In various embodiments, depending on the tolerance of the patient and the goal of the therapist, the knee hinges may be locked in progressive (e.g., incrementally increasing or decreasing) angles such that the static angle is progressively adjusted over time. Accordingly, the user's knee may be gradually accustomed to a static angle, and the static angle may be progressively increased or decreased, according to whether extension or flexion, respectively, is desired.

These configurations are exemplary, and a wide variety of advantageous configurations for various modalities will be made obvious to those of ordinary skill in the art. Various embodiments may, for example, advantageously replace rectangular or otherwise shaped pillows, stacking pillows, and other inconvenient and unwieldy methods of providing ROM exercises.

Foot Plate

In various embodiments, the foot plate may include a platform to receive a human foot, and at least one plate frame member, which removably and adjustably attaches to the lower portion of the stabilizer frame member. In some embodiments, a plurality of plate frame members may be provided, which removably and adjustably attach to the lower portion of the stabilizer frame member(s).

Frame, Extension, Attachment to Knee Stabilizer, Materials, and Construction

The plate frame members may adjustably attach in the sense that the length from the knee hinge of the knee stabilizer to the foot plate is adjustable. In some embodiments, the plate frame members may include open channels, closed channels, tubes, other appropriate members, or some combination thereof, configured to be mated with the attachment points on the distal end of the lower portions of the stabilizer frame members, which may likewise include channels, tubes, other appropriate members, or some combination thereof. In some embodiments, the plate frame members may be integrated together, similarly as disclosed in reference to the knee stabilizer.

In some embodiments, the mating members may slide into each other, such as the plate frame members sliding into the stabilizer frame members such that when the foot plate is removed, uncomfortable or injurious internal channels or edges are not exposed to the user's leg. As disclosed in reference to the knee stabilizer, the plate frame members and mating stabilizer frame members may include, in various embodiments, inner and outer members, substantially identical mating members, other appropriate structures including structures disclosed elsewhere herein, or some combination thereof.

In various embodiments, the foot plate frame members may be integrated together into a unitary structure, such as is discussed in relation to the knee stabilizer. In some embodiments the foot stabilizer may include materials as discussed in relation to the knee stabilizer. In some embodiments, at least some portion of the foot stabilizer may be provided with coatings as discussed in relation to the knee stabilizer.

In some embodiments the foot plate, or some component thereof, may include rubber, metal, steel, aluminum, titanium, polymers, polyvinyl chloride, urethane, other suitable materials, or some combination thereof. In some embodiments the foot plate, or some component thereof, may be provided with at least one coating such as is discussed herein in relation to coating of the knee stabilizer.

Rollers

In various embodiments, the foot plate may include at least one roller and, in some embodiments, a plurality of rollers, designed to receive a human foot. In some embodiments, the rollers may be at least as wide as a foot of an intended user, and may be removably and rotatably attached to the foot plate. The rollers may be rotatably attached at least such that the rollers rotate about their longitudinal axis when a foot is rubbed over them. In various embodiments, the rollers may advantageously enhance ease in gliding a user's foot back and forth over the rollers, and so may advantageously provide for and/or encourage knee glide exercises.

In various embodiments, the rollers may be patterned, coated, textured, or some combination thereof, or otherwise provided with a means of more advantageously gripping the bottom of the foot to encourage rotation of the rollers about the longitudinal axis rather than sliding of the foot across the rollers. In various embodiments, the rollers may include metal, polymers, urethane, rubber, other appropriate materials, or some combination thereof.

In particular the rollers may, in some embodiments, be provided with longitudinal extensions which fit into bosses protruding upwards from the foot plate. In some embodiments, the rollers may be permanently or semi-permanently installed in a bracket which is removably secured to the foot plate, such as by snaps, hook-and-loop fabric, magnets, set screws, other suitable mechanisms, or some combination thereof. In some embodiments, the rollers may rotate in bearings, bushings, or some combination thereof. The bearings, bushings, etc. may, in various embodiments, be located on the roller, in the roller, on a longitudinal extension of the roller, in a longitudinal extension of the roller, in a boss protruding from the foot plate, on a boss protruding from the foot plate, in a bracket receiving the roller, on a bracket receiving the roller, other appropriate configurations, or some combination thereof.

In various embodiments, the rollers may be configured to be removed from the foot plate. The foot play may be configured to safely and comfortably receive the user's foot when the rollers are removed (e.g., sub-surface roller brackets, bosses positioned away from a user's foot, shrouded bosses, or other appropriate protective configuration). The rollers may be configured, for example, to be disposed within one or more bands (e.g., elastic bands) such as, by way of example and not limitation, in one or more pouches in the band(s). The bands may be, for example, conveniently disposed (e.g., wrapped around, clipped around, bucked around, strapped around, slipped over) on a user's appendage (e.g., on an ankle). Various such embodiments may be used, for example, for weight training. Accordingly, various such embodiments may, for example, promote lubrication of the joint capsule and/or combating scar tissue formation.

Foot Platform

In various embodiments the foot plate may include a platform to receive a human foot which, in various embodiments, may be an open frame, a solid platform, a fenestrated platform, an open platform with removable insert plates, other appropriate structures, or some combination thereof. In some embodiments, the platform may be provided with structures to attach the foot rollers thereto, such as bosses, pockets, brackets, receptacles, magnetic areas, ferrous areas for receiving magnetic attachments, one side of hook-and-loop material, other appropriate coupling means, or some combination thereof.

Resistance

In various embodiments, the foot plate may include at least one lower attachment point on or about the platform, and at least one upper attachment point on or about the plate frame stabilizer to attach at least one resistance element. In some embodiments, a plurality of lower attachment points may be provided on or about each side of the platform such that one of the attachment points on each side may be selected for use. Various combinations of attachment points may be selected for different purposes, to provide different levels and different directions of resistance to strengthen or provide therapy to different joints, bones, muscles, tendons, ligaments, etc. In some such embodiments, at least three lower attachment points may be provided on each side of the foot plate platform, either actually on the side of the platform or underneath the side of the platform.

The attachment points may, in various embodiments, be hooks, studs, holes, loops, eyes, grooves (e.g., tracks in a side of the footplate for a continuous resistance element such as an elastic band to be placed into) other appropriate structures, or some combination thereof. In various embodiments, a resistance element may be attached to an upper attachment point and to a lower attachment point; a resistance element may be attached to one lower attachment point, passed through the upper attachment point, and back to the same lower attachment point or to another lower attachment point on the same side of the platform; a resistance element may be attached to an upper attachment point, through or about a lower attachment point on one side, across the platform (e.g. beneath or through it), through or about a lower attachment point on the other side, and up to an upper attachment point, whether the same or another; other appropriate structures and configurations; or some combination thereof.

Various resistance configurations may be chosen, for example, by changing anchor points to affect resistance and isolate, by way of example and not limitation, target muscle groups, ligaments, tendons, joints, or some combination thereof. Therapists may, for example, configure attachments and prescribe specific resistance element configurations. By way of example, and not limitations, specific configurations may target a lateral aspect and/or medial aspect of the lower extremity. For example, if structures in the medial aspect of the knee such as, by way of example and not limitation, the Medius Collateral Ligament (MCL), the vastus medialis obliquus muscle, the sartorius and the adductor magnus tendon, the medial head of the gastrocnemius muscle, the medial patellofemoral ligaments, or some combination thereof, are targeted, the placement of the resistance bands may be oriented in such combination that may increase and isolate to achieve maximum desirable tensile force to the selected region(s). Various embodiments may accordingly be configured to advantageously enable various such closed kinetic chain exercises which may, for example, advantageously combat DVT, post-surgical/post-injury muscle wasting, and/or negative effects of physiological inflammatory response(s).

Additionally, foot exercises with added resistance and/or weights may, for example, also activate important knee muscles, ligaments, and/or tendons such as, by way of example and not limitation, the quadriceps and/or the hamstrings. In various embodiments, specific therapy prescriptions may, for example, also include locking the knee stablizer in one or more angles (e.g., as described above). Various combinations of a predetermined knee angle(s) and predetermined resistance element configuration(s) may, for example, advantageously be used to therapeutically affect the force experienced and/or induced in various targeted structures. Accordingly, various embodiments may, for example, advantageously enable predetermined therapeutic combinations of angles, resistance, and/or motion not achievable by existing devices (such as, for example, attempting to combine knee braces, stacked pillows, and other such devices).

DETAILED DESCRIPTION OF THE DRAWINGS

As with all drawings and specific embodiments presented herein, various other embodiments are disclosed directly or indirectly herein. It should be noted that, where applicable, "left" and "right" refer to a user's perspective while wearing an embodiment under discussion. Furthermore, "left and right component 1 and 2" is a compact notation that can be replaced with "left component 1" and "right component 2." Similarly, "component 1 and 2" is a compact notation that can be replaced with "component 1" and "component 2." Where applicable, in the interest of compactness and clarity, direction (e.g., left and right) can be inferred from the drawings reference or from the context, and may not necessarily be specifically stated for every component or feature.

FIGS. 1-2

Figure 1:
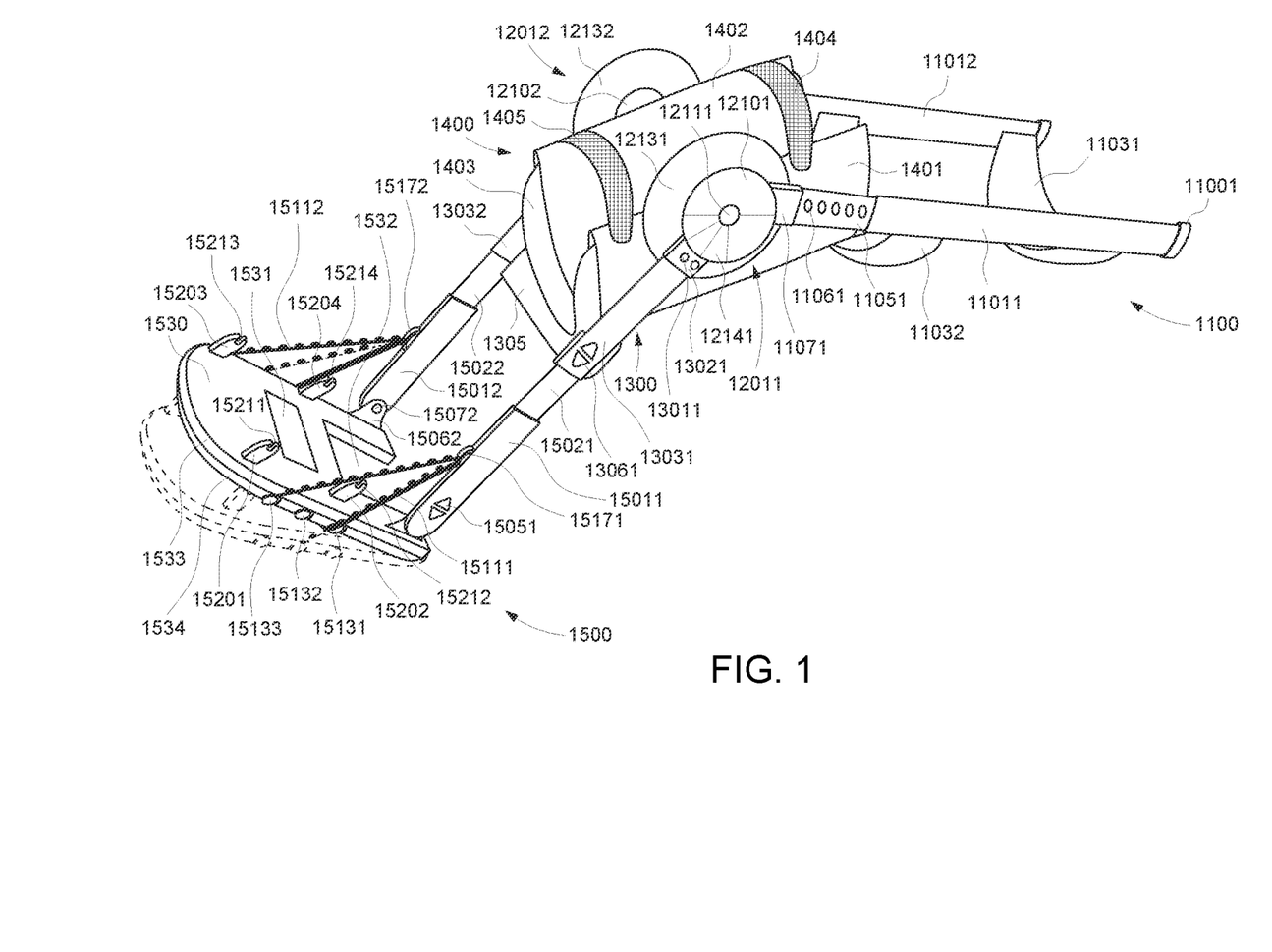
FIG. 1 illustrates an exemplary multi-modal rehabilitation device including a knee stabilizer and foot plate.
Figure 2:
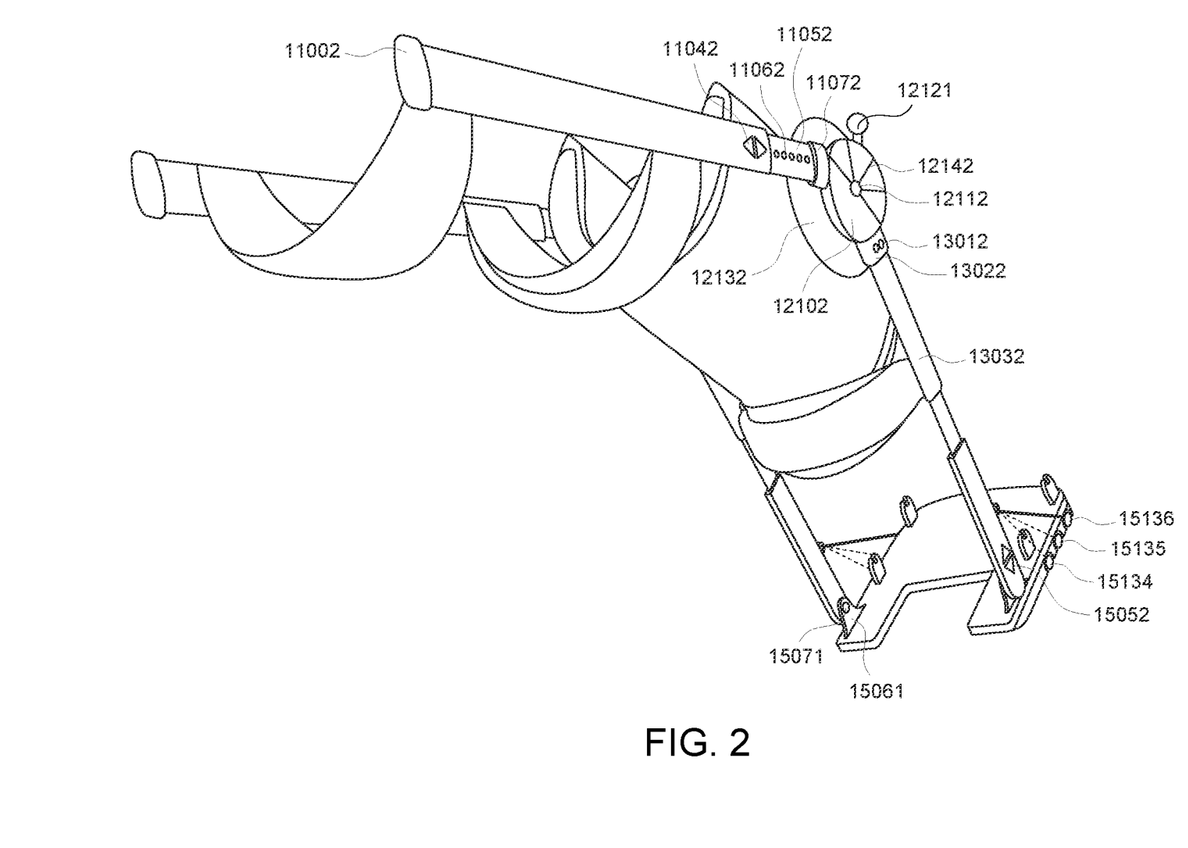
FIG. 2 illustrates another view of the exemplary multi-modal rehabilitation device of FIG. 1.

FIG. 1 illustrates an exemplary multi-modal rehabilitation device including a knee stabilizer and foot plate. FIG. 2 illustrates another view of the exemplary multi-modal rehabilitation device of FIG. 1.

The knee stabilizer includes upper stabilizer 1100, knee hinges 12011 and 12012, and lower stabilizer 1300. It is shown further provided with removable foot plate 1500 and thermal compression pack 1400. Upper stabilizer 1100 includes left and right upper frame members 11011 and 11012, connected together by first upper rear band 11031 and second upper rear band 11032. The upper rear bands may be flexible, rigid, semi-rigid, or some combination thereof. They may be padded, or have padded inserts.

Upper inner frame member 11051 slides inside upper frame member 11011, and is provided with adjustment features 11061. Similarly, upper inner frame member 11052 slides inside upper frame member 11012, and is provided with adjustment features 11062. Arrows 11042 may be, for example, an adjustment lock release (e.g., a push button or a sliding release), an adjustability indicator, or both, and may be, for example, on one side (as shown in FIGS. 1 and 2), on the other side, on both sides, or omitted altogether. Adjustment features may, by way of example and not limitation, be detents or holes with matching locking features (not shown); may be optional, such as with one or more lock screws, lock cams, or other appropriate locking mechanisms; may be positioned on one or more edge instead of on a wide surface; may provide for infinite adjustment (such as with lock screws or flexible grippers under pressure); or some combination thereof. Upper left frame member is covered by cap 11001 and upper right frame member is covered by cap 11002. The caps may be flexible, rigid, or some combination thereof, and may advantageously cushion, protect, or shield a user from the ends of the frame members.

Left and right upper inner frame members 11051 and 11052 are pivotably secured to locking hinge 12011 and 12012, respectively, by left and right upper hinge members 11071 and 11072, respectively. Left and right central hinge features 12111 and 12112, respectively, may be, for example, central pins about which one or more features rotate. Right hinge control feature 12121 may be rotated by a user to lock or unlock the left and right knee hinges 12011 and 12012 or to move transition them into a desired mode. Hinge mechanism 12101 and 12102 bears indicator marks 12141 and 12142 which may, for example, guide a user in moving the hinge control feature (not shown on the left, and 12121 on the right) to the proper orientation for a desired mode. In various embodiments, the hinge control feature may be, for example, a knob, a switch, a lever, or other suitable component, to the proper orientation for a desired mode. In some embodiments, the hinge control feature may be, for example, an inset rotating feature in a center of the outer face of the hinge, a linear sliding feature instead of a rotating feature, a push button, or other appropriate mode selection mechanism.

Hinge cover 12131 separates the user from the primary mechanisms of the hinge, and may protect the user, enhance compression (e.g. of a thermal compression pad), or some combination thereof. The hinge cover may be formed from materials including, but not limited to, foam, rubber, elastomer, neoprene, urethane, or some combination thereof. Similarly, knee hinge 12012 includes knee cover 12132 which separates the user from hinge mechanism 12102.

Lower frame 1300 includes lower frame members 13031 and 13032 connected by lower rear band 1305, which may be configured like the upper rear bands. Lower frame members 13031 and 13032 connect to lower hinge members 13021 and 13022, respectively, being fastened thereto by fasteners 13011 and 13012, respectively. Fasteners 13011 and 13012 may be visible (as shown) or hidden, and may be rivets, bolts, screws, adhesive, detents, weldments, integral connections, or some combination thereof. Other secured locations may be similarly joined.

Foot plate 1500 is removably connected to lower frame 1300. The foot plate frame members 15011 and 15012 include adjustable attachment regions 15021 and 15022. The adjustable attachment regions may be all or part of the foot plate frame members, may be separate components permanently, removably, or adjustably secured to the foot plate frame members, or some combination thereof. The adjustable attachment regions 15021 and 15022 slidably engage in lower frame members 13031 and 1302, respectively. The adjustable attachment regions may slide inside tubular lower frame members (shown), slide over, slide along, snap into, adjustably engage with, or some combination thereof. The adjustable attachment regions may be adjusted and locked as discussed in relation to adjustment of the upper frame. Arrows 13061 may be indicators, decorative features, adjustment release or engagement buttons, or some combination thereof.

Foot plate frame member 15012 is pivotally connected to platform 1530 by hinge pin 15072 and boss 15062. Likewise, frame member 15011 is pivotally connected to platform 1530 by hinge pin 15071 and boss 15061, respectively. Bosses 15061 and 15062 may be omitted and pins 15071 and 15072 directly engage with platform 1530. Pins 15071 and 15072 may be a boss on frame members 15011 and 15012, respectively, or may pass therethrough. Other pivotal connections may be used. The pivotal connection may be provided with a predetermined or adjustable level of friction. Left and right arrows 15051 and 15052 may be similar, for example, to arrows 11042. Arrows 15051 and 15052 may be, for example, indicators, decorative features, pivot adjustment release or locking buttons, or some combination thereof.

Platform 1530 includes bevel 1533 for user comfort, which may be adjusted or omitted, and lower platform 1534, which may be identical with the platform 1530 or may be a separate layer. Apertures 1531 and 1532 may provide airflow and ventilation. Roller supports 15201, 15202, 15203, and 15204 are provided with indents 15211, 15212, 15213, and 15214, respectively. The roller supports may have 'snap-in' indents (shown), locking receivers, holes for one or more pin to pass through per roller, or some combination thereof.

Left resistance element 15111 is a single elastic band that passes through upper attachment point 15171 on frame member 15011, and passes over at least two of lower attachment points 15131, 15132, or 15133. A user may choose which two attachment points to select for the resistance element based on the resistance desired. Similarly, resistance element 15112 passes through upper attachment point 15172 and over at least two lower attachment points 15134, 15135, or 15136. For example, the resistance element may be configured as shown by the middle dashed line, where the band is passed over the middle attachment point instead of the attachment point closer to the toe). resistance elements 15112 and 15111 may be combined into a single structure which passes under or through platform 1530. Attachment points may be hooks, bosses, eyes, buckles, snaps, or some combination thereof. There may be more or less lower attachment points. The resistance element configuration (e.g., which pairs of lower attachment points to use) may be selected, for example, according to a desired resistance pattern. Selection may be, for example, by a user or by a health professional (e.g., a physician, chiropractor, or physical therapist). For example, 15136 and 15135 may be selected on the right, and 15131 and 15132 selected on the left, to provide higher resistance on the right side of the foot in order to, for example, target certain muscles or exercise patterns.

In some embodiments, for example, frame members 15011 and 15012 may join together at a lower end and be coupled to the platform 1530 at a single point such as, for example, by a bi-axial or multi-axial joint (e.g., a 'knuckle' joint or ball and socket joint), to emphasize selective strengthening. In some embodiments, frame members 15011 and 15012 may be slidable, or provided with a control feature that is operable to place them in a slidable configuration, such that, for example, they slide up and down within a range (e.g., without coming off) over lower frame members 150321 and 15022, thereby, for example, allowing greater selective strengthening. In some such embodiments, frame members 15011 and 15012 may be connected to platform 1530 by ball-and-socket joints or other pivotable joints, for example, in order to allow limited rotation of the platform 1530 to provide enhanced foot and leg activity options.

Thermal compression pack 1400 is shown configured to go behind a knee, and includes thermal layer 1403, first cover 1401, second cover 1402, first strap 1404, and second strap 1405. Thermal compression layer 1403 may include thermal gel (such as is used in cold packs, ice packs, or heat packs), re-usable thermal liquid or solid, chemically reactive components to be mixed together to create an endothermic or exothermic reaction, or some combination thereof. The thermal compression layer may further include one or more inflatable or otherwise resizable chambers to adjustably apply compressive pressure to a user's body part. The outer covers may be one piece or multiple pieces, and may include different or the same materials, such as nylon, neoprene, urethane, foam, latex, cotton, other appropriate materials, or some combination thereof. The straps may be buckled, snapped, hook-and-loop fastened, or some combination thereof. The straps may go through a loop and fasten back to themselves, may completely encircle a user's leg, may fasten to a feature on the thermal compression pack, or some combination thereof. The thermal pack may completely or partially surround a user's leg, knee, ankle, or foot. Multiple thermal compression packs may be used. A thermal compression pack may be omitted.

FIG. 3

Figure 3:
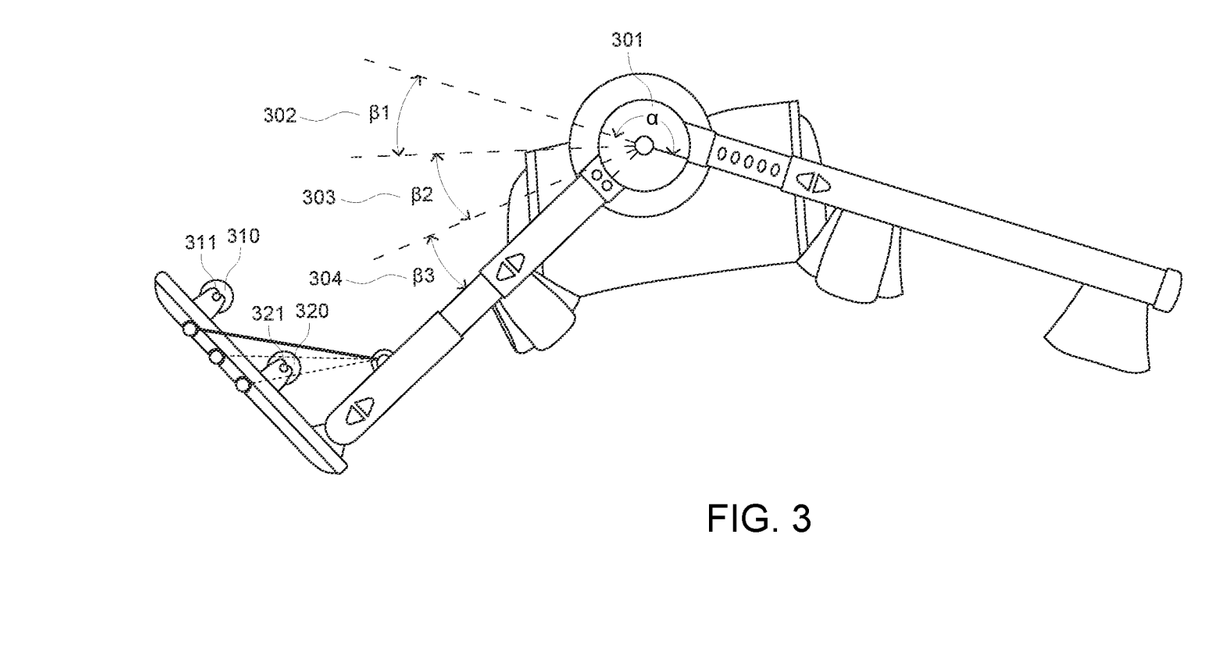
FIG. 3 depicts a side elevation view of an exemplary configuration of the exemplary multi-modal rehabilitation device of FIG. 1.

FIG. 3 depicts a side elevation view of an exemplary configuration of the exemplary multi-modal rehabilitation device of FIG. 1. As shown, hinges 12011 and 12012 may be rotated or locked into multiple angles α 301 relative to a line extending parallel to the upper frame 1100. The hinges may be rotated or locked such that the lower frame 1300 and the foot plate 1500 may rotate freely, or may be locked into multiple angles relative to the upper frame 1100. In the depicted example, the hinges may be, for example, first locked such that a user's knee is angled by approximately β1 degrees 302.

After a given period of time, the hinges may be released and relocked such that the user's knee is angled by an additional β2 303 degrees, such that the user's knee is now at an angle of approximately β1+β2 degrees. After a given period of time, the hinges may be released and relocked such that the user's knee is angled by an additional β3 304 degrees, such that the user's knee is now at an angle of approximately β1+β2+β degrees. The hinges may, for example, be placed in a free-rotation mode such that the lower frame 1300 can rotate freely through a range of angles. The hinges may be placed into one of a variety of predetermined angles such that, for example, the user's leg and knee may be placed into a comfortable but secure position to, for example, sit, stand, lay down and rest their leg.

In various embodiments, hinges may be provided with rotational resistance in at least one selectable free-rotation mode such that, for example, a user may be provided with advantageous exercise options. In some such embodiments, the level of rotational resistance may be adjustable. Rotational resistance may be provided, by way of example and not limitation, by friction pads, and may be adjusted, for example, by tensioning a friction pad against a rotating element.

In the exemplary embodiment depicted, the foot plate 1500 is provided with first roller 310 and second roller 320, each roller having left cylindrical bosses 311 and 321, respectively, and right cylindrical bosses (not shown). The first roller 310 rests in roller supports 15201 and 15203, and are rotatably secured therein by the cylindrical bosses being 'snapped' into indents 15211 and 15213. The second roller 321 likewise rests in roller supports 15204 and 15202, being rotatably secured therein by the cylindrical bosses being 'snapped' into indents 15214 and 15212. In various embodiments, the rollers may be rotatably secured to the platform by, for example, pins, removable or integrated bosses provided with protrusions which rotatably mate with cavities in the rollers, or other appropriate rotatable connection means.

In some embodiments, the rollers may be, for example, textured, padded, smooth, heated, cooled, or some combination thereof. In some embodiments, the rollers may be advantageously used, for example, to 'massage' the bottom of a foot as a user rolls their foot back and forth across them. The rollers, roller supports, or a combination thereof, may, for example, provide rotational resistance to provide, for example, advantageous exercise options. The rollers may, for example, be removed from the platform to allow the user to rest their foot on the platform without the rollers. The rollers may, for example be stowed on or about the platform, the lower frame, the upper frame, or some combination thereof. The rollers may, for example, be used as weights such as, by way of example and not limitation, strapped around a lower leg (e.g., for isotonic knee weight training).

FIG. 4

Figure 4:
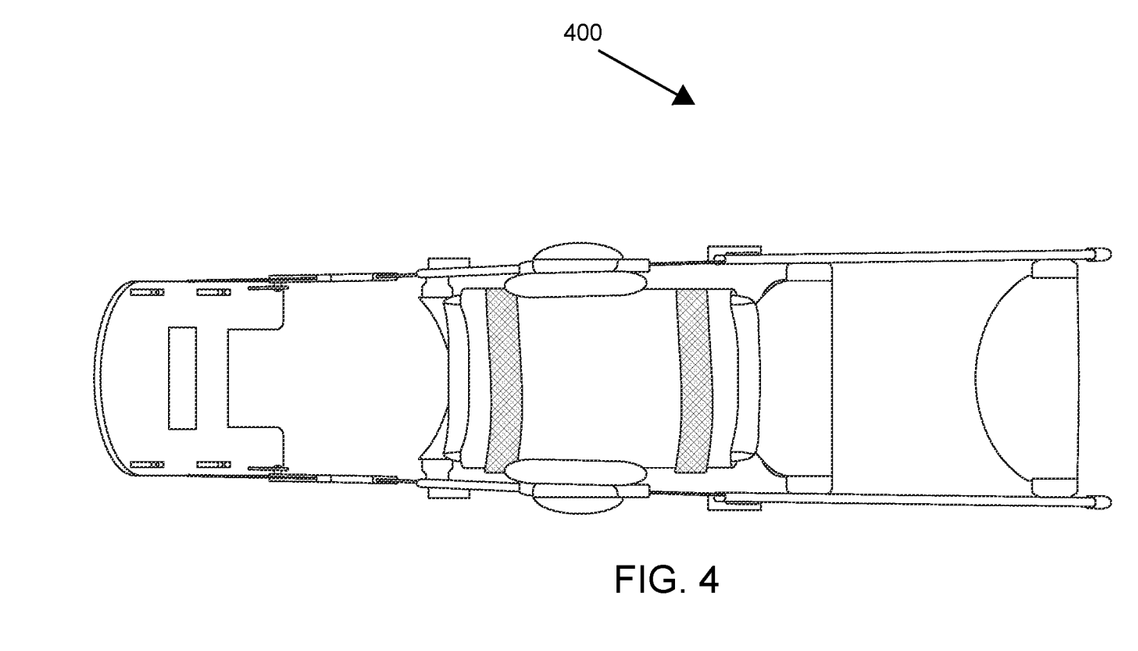
FIG. 4 depicts a top plan view of the exemplary multi-modal rehabilitation device of FIG. 1.

FIG. 4 depicts a top plan view of the exemplary multi-modal rehabilitation device of FIG. 1. The multi-modal rehabilitation device 400 is shown without rollers on the foot plate, and having a thermal pack positioned such that it would wrap around the back of the user's knee when the user places their leg in the device 400.

FIGS. 5-6

Figure 5:
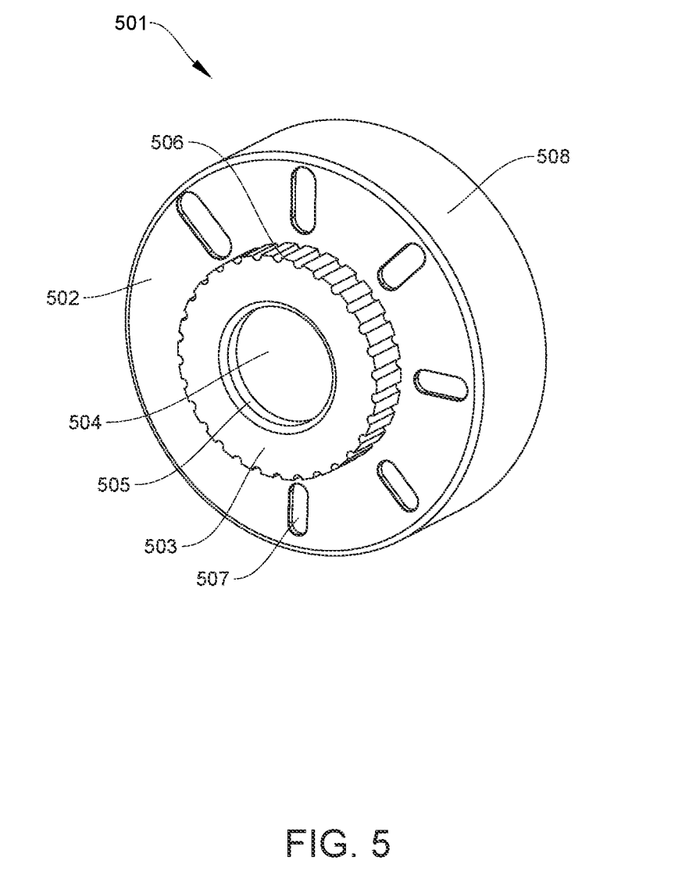
FIG. 5 depicts an exemplary vent control mechanism for a thermal-compression pack.
Figure 6:
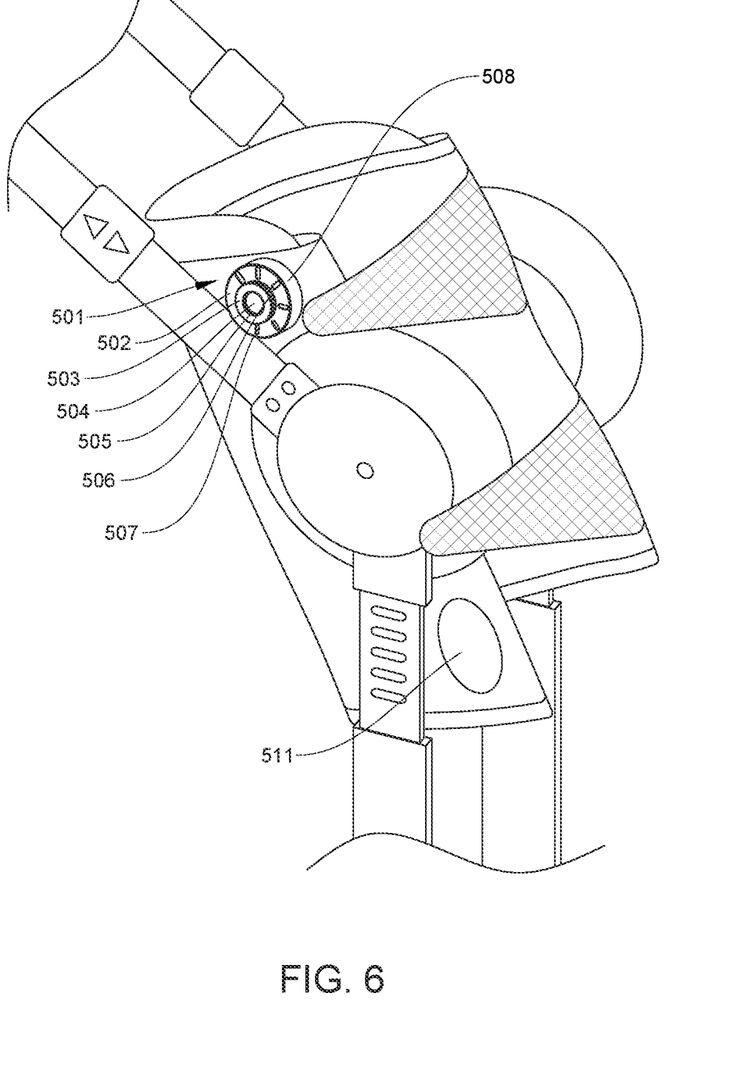
FIG. 6 depicts an exemplary thermal-compression pack in an illustrative use case.

FIG. 5 depicts an exemplary vent control mechanism for a thermal-compression pack. FIG. 6 depicts an exemplary thermal pack in an illustrative use case. In various embodiments, the thermal pack may be inflated, and may be deflated in a controlled manner by a vent control mechanism. The depicted exemplary vent control mechanism 501 is provided with a base 508, which may be connected to a thermal pack. Cover 502 may rotate relative to the base 508 such that apertures 507 are progressively opened to release pressure from the thermal pack. In some embodiments, the cover 502 may be attached to a thermal pack, and base 508 rotates relative to the cover 502. In some embodiments, the base 508 may be rotated, for example, by operation of the knob 503, which is provided with grip pattern 506 which may, for example, facilitate a user gripping the knob 503. The grip pattern may, for example, be any suitable pattern or be omitted altogether. Threads 505 may be used, for example, to attach a filling mechanism which may, for example, depress central portion 504. Threads may be omitted in some embodiments. Central portion 504 may be spring-actuated, for example, may be a plunger that opens when the knob 503 is operated in an opening direction such that threads 505 move the plunger back or forwards, may be omitted, or some combination thereof.

Optional integrated pump 511 may be, for example, disposed within the thermal-compression pack, and be activated, for example, by touch, by predetermined parameters (e.g., by pressure level such as to maintain a specific pressure for a specific duration of time, or by time such as to provide a predetermined level of pressure at predetermined time intervals), by an external control device (e.g., a portable personal device provided with a set of program instructions such as a smartphone, tablet, or computer with an app or program, or a dedicated or multi-purpose remote control device). The pump 511 may be removable or detachable.

The vent control mechanism may be used to vary, for example, the rate at which an inflatable thermal pack deflates. The thermal-compression pack may, for example, be inflated to provide compression to a user's body portion (e.g., a knee, a leg portion, a foot portion, or an ankle), and at least one vent control mechanism operated to allow a controlled release of pressure. Embodiments provided with a mechanism for deflating may, for example, advantageously limit the duration of time which compression is applied and may, therefore, prevent deleterious effects from excessive or unduly prolonged pressure. Providing a vent control mechanism may, for example, advantageously balance safety (e.g., limiting duration of compression) and therapy (e.g., varying the rate of release).

As shown in FIG. 6, the vent control mechanism may be provided on an inflatable housing as part of a thermal pack which may be used for both thermal therapy (e.g., heat, cold), and compression therapy. In some embodiments, the pack may be, for example, only a compression pack, or has independent thermal and compression compartments, at least one of which may be unused. In some such embodiments, at least one of the independent thermal and compression compartments may be removed (e.g., removed from an outer jacket, unzipped, unsnapped, unbuttoned, magnetic elements separated, or hook-and-loop tape detached).

FIGS. 7A-7B

Figure 7A:
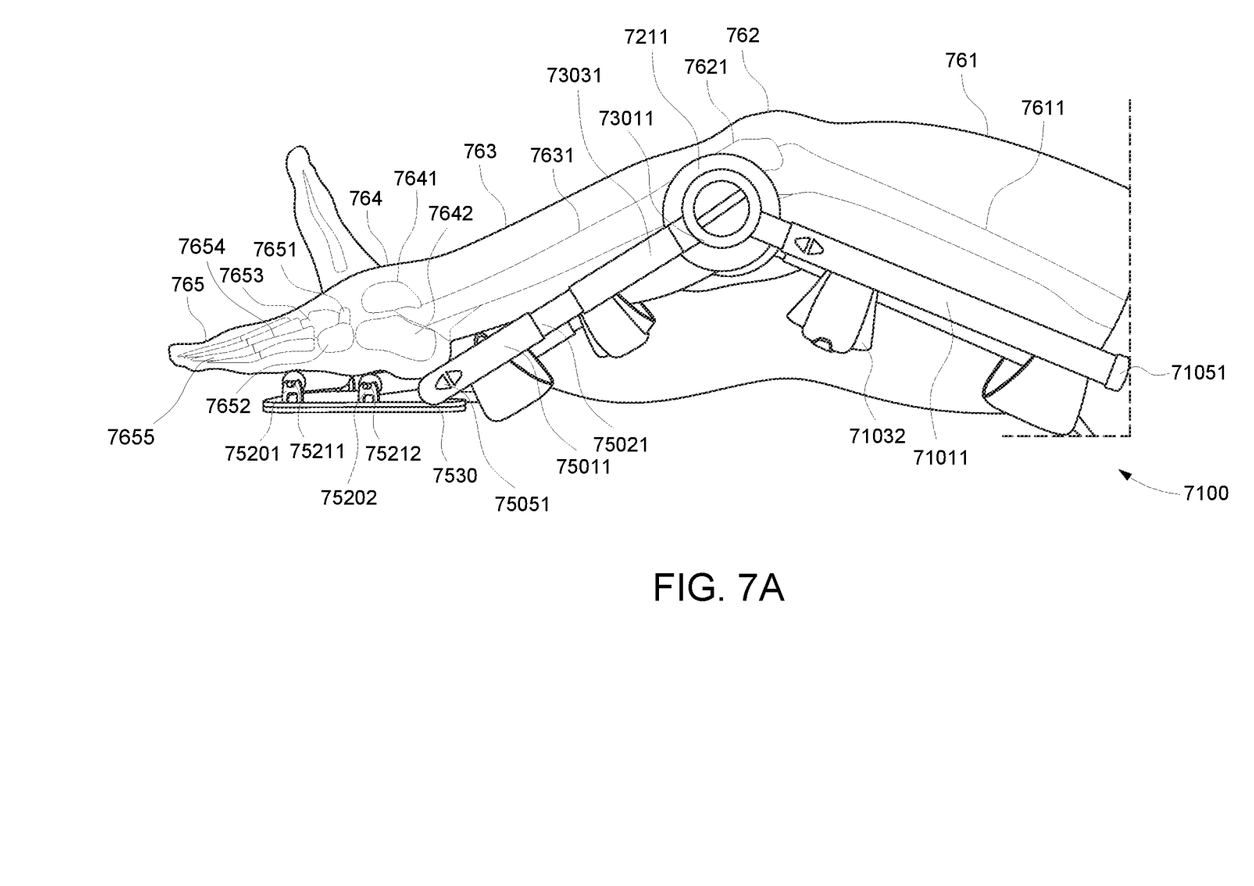
FIG. 7A depicts an exemplary multi-modal rehabilitation device in a first illustrative use case.
Figure 7B:
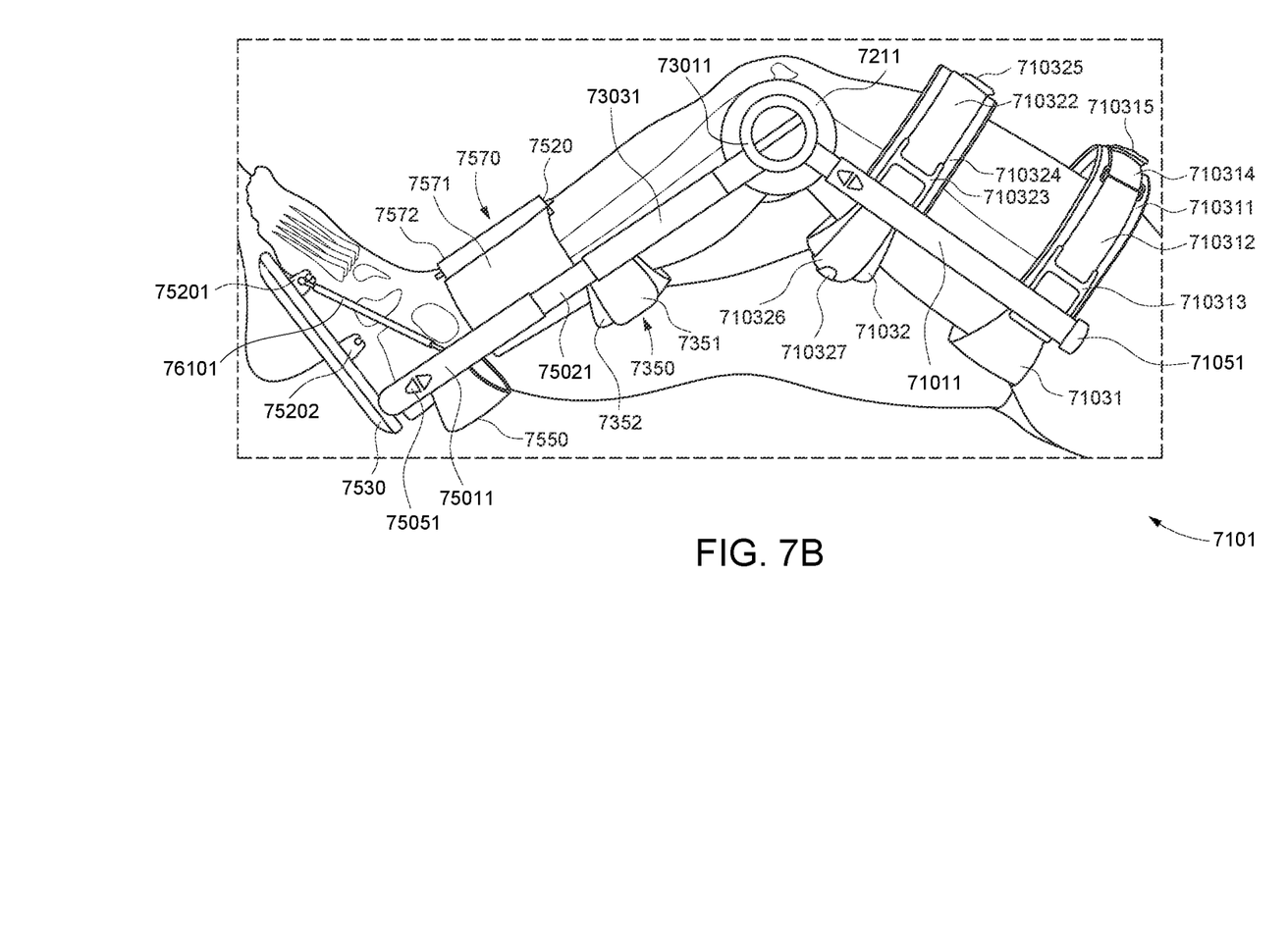
FIG. 7B depicts an exemplary multi-modal rehabilitation device in a second illustrative use case.

FIG. 7A depicts an exemplary multi-modal rehabilitation device in a first illustrative use case. FIG. 7B depicts an exemplary multi-modal rehabilitation device in a second illustrative use case. In illustrative use case 7100 in FIG. 7A, a user's leg is resting in a multi-modal rehabilitation device such that upper leg 761 is positioned in an upper frame, and lower leg 763 is positioned in a lower frame, such that femur 7611 is approximately parallel to upper frame member 71011 and tibia 7631 is approximately parallel to lower frame member 73031. stabilizers 71031, 710326, 7351, and 7550 connect left and right frame members. Straps 710326 and 7351 are provided with pads 71032 and 7352, respectively. Element 710327 may be, for example, a flexible bumper or a label. Straps 710326 and 7351 may be, for example, rigid, and 71031 and 7550 may be, for example, semi-rigid or flexible. Releasable straps may, for example, be provided to secure the user's upper leg 761 to upper frame 71011.

The user's knee 762 and knee cap 7621 are approximately aligned with hinge 7211. Hinges 7211 are provided with hinge control mechanisms 73011 which may be used, for example, to lock and unlock rotation of the hinges, or to lock the hinges into various predetermined angles or ranges of angles. User's foot 765 is flexed at ankle 764, with talus 7641, calcaneus 7642, tarsals 7651, 7652, and 7653, metatarsals 7654, and phalanges 7655 aligned as shown. The user may, for example, be performing a combination foot massage therapy and free motion exercise by rolling the foot 765 forward and backwards over the rollers 75211 and 75212 rotatably secured by roller supports 75201 and 75202 on the platform 7530 of the foot plate 75011. The foot plate 75011 is attached to lower frame 73031 by engaging with lower frame attachments 75021. Arrows 75051 may, for example, be used to unlock, reposition, or adjust the amount of engagement of the foot plate 75011 with the attachment 75021, the angle of of the platform 7530 relative to the lower frame 75031, other appropriate adjustment, or some combination thereof. Ends of frame 71011 are provided with caps 71051 which may, for example, protect the user from the end of the frame members.

At least the user's lower leg 763 is unrestrained, but the multi-modal rehabilitation device may advantageously support the user's upper leg 761 and knee 762. The device may also, for example, limit the range of motion according to the angle at which the hinges 7211 are fixed. In some configurations, the user's upper leg 761 and lower leg 762 may be secured (e.g., by straps) to the upper frame 71011 and lower frame 73031, respectively, and the hinges 7211 be placed in free-rotation mode. The user may then sit, for example, and move their lower leg back and forth to exercise the knee 762. In some configurations, the user may instead lock the knee at a first angle, and may, over time, progressively increase or decrease the angle by increments in order to increase the range of motion. Such configurations may, for example, be advantageously used in rehabilitation after surgery or injury.

In scenario 7101, the user upper leg is strapped into upper frame 71011, no rollers are in foot plate platform 7530, resistance elements 76101 are installed, and rollers 7520 are disposed in band 7570 which is disposed just above user's ankle. The multi-modal rehabilitation device may, for example, be configured for foot resistance exercises, for the user to sit in a chair and perform free motion exercises, for compression therapy, or some combination thereof.

A first upper strap includes hardware 710313, straps 710312 and 710314, closure 710315, and padding 710311. A second upper strap similarly includes hardware 710323, strap 710322, closure 710325, and cushion 710324. The cushions may be one or two pieces, and may be fastened, or may be at least partially attached to one or more straps. The straps may be, for example, webbing (e.g., nylon or polyester), vinyl, urethane, or some combination thereof. The hardware may be for example, buckles, or retainer hardware over which the straps are looped and secured. The closure may be, for example a buckle, or a length of a strap passed through a retainer (not shown) and doubled back to engage, for example, a fastener. A fastener may include, for example, hook-and-loop material, snap, or magnet.

The user's foot is resting directly on platform 7530. resistance elements 76101 are attached to roller supports 75201 at one end and to a frame of the foot plate at the other end. The resistance elements 76101 may, for example, be a barrel with at least one spring-loaded end, or an elastic band. The resistance elements may be attached on one or both sides of the platform 7530 to roller support 75202, or to dedicated attachment points. Depending on the resistance elements used and the attachment points selected to attach them to on each side of the foot, advantageous exercise therapy may be provided.

Repositionable band 7570 is disposed on the user's lower leg just above the ankle. The band 7570 may, for example, an elastic strap and may, for example, be advantageously employed as a compression device, as a weight-holding device, or some combination thereof. Weights 7520, which may, for example, be implemented as rollers 75211 and 75212 in scenario 7100, are disposed in sleeves 7572 in the strap 7570. The band body 7571 may, for example, be webbing, neoprene, elastic fabric, other appropriate material, or some combination thereof. The band may, for example, be slid over the user's foot, may be fastened around the user's leg, or may be, a pre-loaded "C" shape which may be expanded placed around the user's leg, and allowed to 'spring' snug around the leg. In some configurations, the band may be placed anywhere along the upper or lower leg, may be positioned elsewhere on the user's body, or may be removed. The weights may, for example, advantageously provide weight to enhance strengthening or range of motion exercise therapies.

FIG. 8

Figure 8:
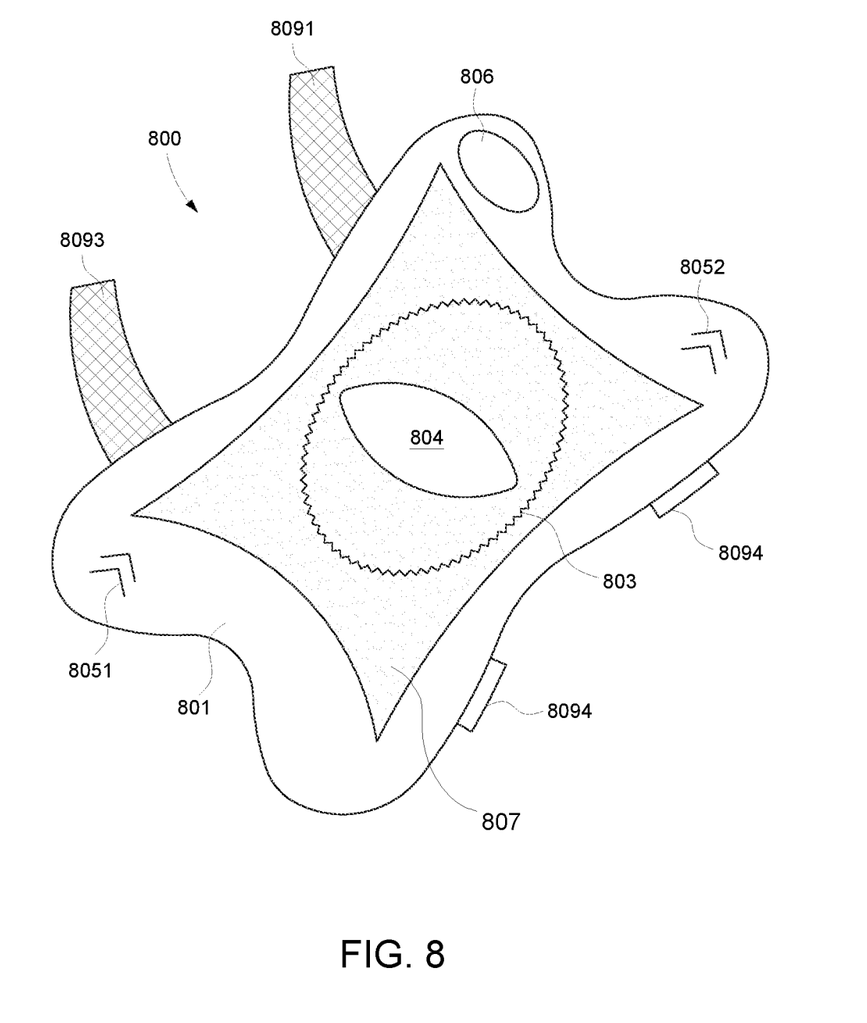
FIG. 8 depicts an exemplary thermal-compression pack.

FIG. 8 depicts an exemplary thermal-compression pack. Thermal compression pack 800 is provided with inflatable housing 801, which may be inflated at inflation region 806. Inflation region 806 may, for example, be an embedded or integrated pump, or a connection or inflation point for an external pump. Inflatable housing may be wrapped around a body portion of a user (e.g., a knee, a leg, an ankle, a foot, or some other body portion), secured by engaging first fastener strap 8091 and second fastener strap 8093 with attachment points 8094. The fastener straps and attachment points may engage, for example, as hook-and-loop fasteners, straps, magnets, buckles, or other suitable fastening mechanisms.

Once wrapped around a body portion of a user, for example, the inflatable housing 801 may be inflated to a desired pressure (e.g., by reading a pressure gauge (not shown), by inflating for a predetermined amount of time, or by manually monitoring inflation to a desired point). The inflatable housing may thereby advantageously provide compression therapy to the portion of the user's body to which it is applied. The inflatable housing is provided with first and second slow air release apertures 8051 and 8052, respectively. The air release apertures may, for example, be static release vents configured to provide a static size pressure escape. The vents may, for example, be slits of a predetermined size and shape to allow a predetermined flow of air (or other suitable fluid) out of the inflatable housing 801. In some embodiments, the air release apertures may be adjustable (e.g., to release compression in increments of desired time such as, by way of example and not limitation, 15, 30, 45, 60 minutes, or other desired timer interval), such as is disclosed in relation to FIGS. 5-6.

Thermal insert 807 may, for example be a pack which may be pre-heated or pre-chilled (e.g., in a refrigerator, filled with ice, a disposable multi-part thermal pack, warmed in a microwave oven or in an oven or hot water bath, or other suitable heating or cooling method). The thermal insert may, by way of example and not limitation, gel, liquid, solid, or gas. The thermal insert may be, for example, disposable or reusable. The thermal insert may, for example, be removable or fixed to the inflatable housing. A removable thermal insert may, for example, be disposed within a pouch, or fastened to the inflatable housing (e.g., by hook-and-loop, snap, magnet, or strap).

Elastic band 803 is provided which may, for example, be in the thermal insert or in the inflatable housing. The elastic band may be, for example, sewn into the thermal compression device, or attached thereto. The elastic band may advantageously, for example, enhance fit by 'puckering' a central region of the device which may then expand to fit snugly over, against, or around a body portion as the device is fastened snugly in place.

In various embodiments, the housing may be used, by way of example and not limitation, to secure one or more electrodes for electrical muscle stimulation (EMS) and/or transcutaneous electrical nerve stimulation (TENS) units. Various embodiments, for example, may advantageously provide for application of EMS and/or TENS to a portion of a user body such as, for example, a leg. In some such embodiments, stimulation may be applied during application of thermal and/or compressive therapy, when thermal and/or compressive therapy is not being applied (e.g., with an expended thermal pack or no thermal pack, when no compression is applied), or some combination thereof. Accordingly, various such embodiments may achieve benefits such as, by way of example and not limitation, reducing post-surgical pain, disbursing swelling, and/or aiding in healing.

Aperture 804 is provided in the thermal-compression device. The aperture may, for example, be entirely through all layers of the thermal-compressive device. The aperture may advantageously enhance bending to promote fit around a body portion (e.g., a knee, heel, or ankle). The aperture may, for example, be elastic, may be stitched through multiple layers to provide a closed seam bordering the aperture, or some combination thereof.

CONCLUSION

The claimed subject matter has been herein disclosed sufficiently for persons skilled in the art to comprehend and practice. The various embodiments, examples, and illustrations disclosed herein, while representing the best and various alternative modes of carrying out the the claimed subject matter as currently contemplated by the inventors, are by no means limiting or exhaustive, but serve as an aid to comprehending the full nature and scope of the claimed subject matter. Various other embodiments will become apparent which fall within the scope of this disclosure and claims.

I claim:

1. A multi-modal rehabilitation device comprising:
   a multi-position knee stabilizer comprising a stabilizer frame member comprising an upper portion, a lower portion, and a lockable hinge joining the upper portion and lower portion;
   a foot plate comprising:
      a foot plate frame member configured to removably and adjustably attach to a distal end of the lower portion of the stabilizer frame member, and
      a platform rotatably coupled to the foot plate frame member;
   a resistance element releasably coupled to the foot plate frame member and the platform and configured to adjustably resist rotation of the foot plate in a first rotational direction; and
   a means for connecting the knee stabilizer to a human leg;
   wherein the lockable hinge is configured to operate in at least two user-selectable modes: an unlocked mode in which the hinge rotates freely, and a locked mode in which the hinge is held in one of a plurality of predetermined static positions.

2. The device of claim 1, wherein:
   the knee stabilizer further comprises a second stabilizer frame member comprising a second upper portion, a second lower portion, and a second hinge joining the second upper portion and the second lower portion;
   the foot plate comprises a second foot plate frame member configured to removably and adjustably attach to a distal end of the second lower portion of the second stabilizer frame member;
   the platform is further rotatably coupled to the second foot plate frame member; and
   the knee stabilizer frame member and the second stabilizer frame member are connected by at least a first lateral element and a second lateral element.

3. The device of claim 1, wherein the platform further comprises a plurality of rollers configured to rotate when a human foot is passed thereover.

4. The device of claim 3, wherein the rollers are releasably coupled to the platform.

5. The device of claim 3, further comprising a band provided with at least one pocket configured to receive at least one of the rollers,
   wherein the band is configured to be removably secured around a human leg.

6. The device of claim 1, wherein the foot plate further comprises:
   a plurality of resistance element attachment points on a left side and on a right side of the platform, and
   at least one resistance element attachment point on the foot plate frame member.

7. The device of claim 6, further comprising, wherein the resistance element connects at least one resistance element attachment point on the platform to the at least one resistance device attachment point on the foot plate frame member.

8. The device of claim 6, wherein the resistance element comprises an elastic band.

9. The device of claim 1, wherein the platform is lockably rotatable relative to the first foot plate frame member and second foot plate frame member.

10. The device of claim 1, wherein the lockable hinge is further configured to operate in a third user-selectable mode being a resistance mode in which the hinge is unlocked but resists rotation.

11. The device of claim 10, wherein the lockable hinge comprises a resistance adjustment selector configured to alter a level of resistance against rotation when the lockable hinge is operated in the resistance mode.

12. The device of claim 1, further comprising a removable and relocatable self-venting thermo-compressive device, the thermo-compressive device comprising:
   an inflatable housing with at least one release vent therein,
   a flexible thermal insert disposed at least partially within the inflatable housing, and
   an aperture placed in a substantially central region of the housing, and passing through an entire thickness of the thermo-compressive device; and
   wherein the thermo-compressive device is:
      configured to be removable and relocatable, and
      is adapted to be removably secured against at least some portion of a human leg.

13. The device of claim 12, wherein the at least one release vent is a non-adjustable static-release vent.

14. The device of claim 13, wherein the at least one static-release vent comprises a slit in the inflatable housing.

15. A method for rehabilitating a human knee, the method comprising:
   providing a multi-modal rehabilitation device comprising:
      a multi-position knee stabilizer comprising a stabilizer frame member comprising an upper portion, a lower portion, and a lockable hinge joining the upper portion and lower portion,
      a foot plate comprising:
         a foot plate frame member configured to removably and adjustably attach to a distal end of the lower portion of the stabilizer frame member, and
         a platform rotatably coupled to the foot plate frame member,
      a resistance element releasably coupled to the foot plate frame member and the platform and configured to adjustably resist rotation of the foot plate in a first rotational direction, and
      a means for connecting the knee stabilizer to a human leg,
   wherein the lockable hinge is configured to operate in at least two user-selectable modes: an unlocked mode in which the hinge rotates freely, and a locked mode in which the hinge is held in one of a plurality of predetermined static positions;
   aligning the multi-position knee stabilizer such that the stabilizer frame member is oriented in a plane parallel to a sagittal plane of a leg of a patient;
   releasably coupling the knee stabilizer to the leg of the patient such that the lockable hinge is adjacent to a knee of the leg, the upper portion of the stabilizer frame member is proximal to the lockable hinge, and the lower portion of the stabilizer frame member is distal to the lockable hinge.

16. The method of claim 15, further comprising:
selecting the unlocked mode, and
rotating a lower extremity of the leg relative to the knee.

17. The method of claim 15, further comprising:
selecting the unlocked mode, and
rotating a lower extremity of the leg relative to the knee to place the user's knee in a desired degree of flexion, and
selecting the locked mode.

18. The method of claim 15, further comprising:
rotatably coupling a plurality of rollers to the platform, and
cyclically rotating a lower extremity of the leg relative to the knee in a forward direction followed by a backward direction such that a bottom of a foot of the leg rotatably engages the plurality of rollers.

19. The method of claim 15, further comprising:
adjusting the resistance element into at least one combination of predetermined attachment points on the foot plate and the foot plate frame member such that the resistance element resists plantar flexion of a foot of the leg, and
inducing cyclical dorsiflexion and plantar flexion of the foot.

20. The method of claim 19, wherein the resistance element is adjusted into a combination of predetermined attachment points such that the resistance element provides a greater level of resistance to plantar flexion on a selected one of: a medial side of the foot or a lateral side of the foot, relative to the unselected side.

* * * * *